United States Patent
Nakamura et al.

(10) Patent No.: US 8,658,713 B2
(45) Date of Patent: *Feb. 25, 2014

(54) BONE CEMENT COMPOSITION AND PRODUCTION METHOD THEREOF, AND KIT FOR PRODUCING THE SAME

(75) Inventors: Takashi Nakamura, Kyoto (JP); Koji Goto, Kyoto (JP); Takehiro Shibuya, Otsu (JP); Yoshimichi Ueda, Kusatsu (JP); Tokuo Suita, Kusatsu (JP); Hiroaki Nishii, Kusatsu (JP)

(73) Assignees: Kyoto University, Kyoto (JP); Ishihara Sangyo Kaisha, Ltd., Osaka (JP)

( * ) Notice: Subject to any disclaimer, the term of this patent is extended or adjusted under 35 U.S.C. 154(b) by 176 days.

This patent is subject to a terminal disclaimer.

(21) Appl. No.: 13/202,850

(22) PCT Filed: Feb. 23, 2010

(86) PCT No.: PCT/JP2010/052702
§ 371 (c)(1),
(2), (4) Date: Oct. 3, 2011

(87) PCT Pub. No.: WO2010/098304
PCT Pub. Date: Sep. 2, 2010

(65) Prior Publication Data
US 2012/0046385 A1 Feb. 23, 2012

(30) Foreign Application Priority Data

Feb. 25, 2009 (JP) .................................. 2009-041976
Jun. 15, 2009 (JP) .................................. 2009-142130

(51) Int. Cl.
*A61F 2/28* (2006.01)
*C08K 3/22* (2006.01)

(52) U.S. Cl.
USPC .......................................... 523/116; 524/847

(58) Field of Classification Search
USPC .......................................... 523/116; 524/847
See application file for complete search history.

(56) References Cited

U.S. PATENT DOCUMENTS

| | | | |
|---|---|---|---|
| 6,160,033 A | 12/2000 | Nies | |
| 7,498,363 B2 * | 3/2009 | Bublewitz et al. | ............ 523/109 |
| 2007/0048382 A1 | 3/2007 | Meyer et al. | |
| 2007/0213425 A1 | 9/2007 | Higham et al. | |
| 2009/0239970 A1 | 9/2009 | Rodrigues et al. | |
| 2012/0035296 A1 | 2/2012 | Nakamura et al. | |

FOREIGN PATENT DOCUMENTS

| | | | |
|---|---|---|---|
| JP | 2000-86419 A | | 3/2000 |
| JP | 2000-245821 A | | 9/2000 |
| JP | 2000-254220 A | | 9/2000 |
| JP | 2001-503290 A | | 3/2001 |
| JP | 2004-201869 | * | 7/2004 |
| JP | 2004-201869 A | | 7/2004 |
| JP | 2007-54369 A | | 3/2007 |
| JP | 2007-054619 | * | 3/2007 |
| JP | 2007-54619 A | | 3/2007 |
| WO | WO 2006/123589 A1 | | 11/2006 |
| WO | WO 2007/025633 A2 | | 3/2007 |

OTHER PUBLICATIONS

International Search Report dated Apr. 6, 2010 issued in International Appln. No. PCT/JP2010/052702.
Yohji Imai et al.: Characterization of Powder Components of Commercial Bone Cements, Dental Materials Journal, 20(4); 2001, pp. 345-352.
Rodrigues D.C. et al.: Pseudoplasticity and Setting Properties of Two-Solution Bone Cement Containing Poly(methyl methacrylate) Microspheres and Nanospheres for Kyphoplasty and Vertebroplasty, Journal of Biomedical Materials Research, Apr. 2009; vol. 91B; No. 1; pp. 248-256.

* cited by examiner

*Primary Examiner* — Tae H Yoon
(74) *Attorney, Agent, or Firm* — Holtz Holtz Goodman & Chick PC

(57) ABSTRACT

A bone cement composition which contains titanium dioxide particles having a median diameter of 0.5 to 7.0 μm as measured by a laser diffraction/scattering particle size distribution analyzer and a BET specific surface area of 0.5 to 7.0 $m^2/g$ as measured by a nitrogen adsorption method, and a base-forming component comprising a (meth)acrylate polymer and a (meth)acrylate monomer, wherein the content of the titanium dioxide particles is 5 to 50% by mass based on the total mass of the composition. The bone cement composition has bioactivity and is capable of forming a hardened material having a high mechanical strength.

22 Claims, 1 Drawing Sheet

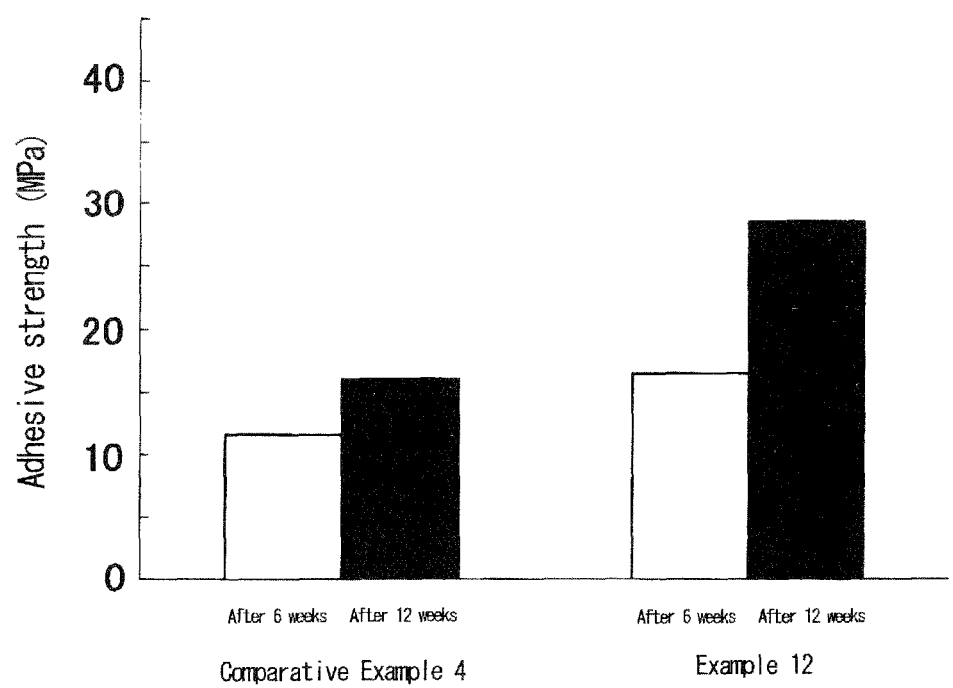

BONE CEMENT COMPOSITION AND PRODUCTION METHOD THEREOF, AND KIT FOR PRODUCING THE SAME

This application is a U.S. National Phase Application under 35 USC 371 of International Application PCT/JP2010/052702 filed Feb. 23, 2010.

TECHNICAL FIELD

The present invention relates to a bone cement composition, a bone cement composition kit, and a bone cement formed material and a production method thereof, and particularly to a bioactive bone cement composition having apatite-forming ability under an environment of a body fluid and a bone cement composition kit for obtaining the bone cement composition, and a bone cement formed material obtained by forming the bone cement composition and a production method thereof.

BACKGROUND ART

A bone cement composition has heretofore been widely used in the world as a bone prosthetic material for a defective part of a bone or an adhesive for fixing a metallic prosthesis such as a hip joint prosthesis to its surrounding bones. A polymethyl methacrylate (PMMA)-based bone cement composition has been most commonly used.

However, the PMMA-based bone cement composition heretofore used has biocompatibility, but does not have bioactivity, i.e., bone-bonding ability to be bonded to a bone, so that when the composition is used as an adhesive for fixing a prosthesis to its surrounding bones in particular, the adhesive separates from the surrounding bones when a long period of time has elapsed from the application thereof, resulting in causing a problem that looseness occurs between the prosthesis and the bones.

Thus, there is proposed a composition with titanium dioxide particles added to the PMMA-based bone cement composition for the purpose of imparting the bioactivity thereto (see, for example, Patent Literature 1).

However, such a PMMA-based bone cement composition containing titanium dioxide particles involves a problem that mechanical strength practically required, specifically, such strength that flexural strength measured according to the measuring method based on ISO 5833 is at least 60 MPa, is not achieved though the bioactivity is achieved.

PRIOR ART LITERATURE

Patent Literature

Patent Literature 1: Japanese Patent Application Laid-Open No. 2007-54619

DISCLOSURE OF THE INVENTION

Technical Problem

The present invention has been made on the basis of the foregoing circumstances and has as its object the provision of a bone cement composition and a bone cement composition kit for obtaining the bone cement composition, which have bioactivity and capable of forming a hardened material having high mechanical strength practically required.

Another object of the present invention is to provide a bone cement formed material having both bioactivity and high mechanical strength practically required and a production method thereof.

Solution to Problem

A bone cement composition according to the present invention comprises titanium dioxide particles having a median diameter of 0.5 to 7.0 μm as measured by a laser diffraction/scattering type particle size distribution analyzer and a BET specific surface area of 0.5 to 7.0 $m^2/g$ as measured by a nitrogen adsorption method, and a base-forming component comprising a (meth)acrylate polymer and a (meth)acrylate monomer, wherein the content of the titanium dioxide particles is 5 to 50% by mass based on the total mass of the composition.

In the bone cement composition according to the present invention, the median diameter and BET specific surface area of the titanium dioxide particles may be preferably 1.5 to 7.0 μm and 0.5 to 5.0 $m^2/g$, respectively.

In the bone cement composition according to the present invention, the titanium dioxide particles may preferably have the following characteristics:
(1) the particles are rutile-type titanium dioxide particles;
(2) the particles are spherical;
(3) the particles are those subjected to an acid-washing treatment; and
(4) the particles are those produced by going through the steps of subjecting a slurry of titanic acid to a spray drying treatment, thereby obtaining dried granules, and subjecting the dried granules to a calcinating treatment.

In the bone cement composition according to the present invention, the content of the (meth)acrylate polymer making up the base-forming component may be preferably 30 to 80% by mass based on the total mass of the base-forming component.

The bone cement composition according to the present invention may preferably comprise a polymerization initiator.

The bone cement composition according to the present invention may be preferably hardened by polymerizing the (meth)acrylate monomer in vivo.

A bone cement composition kit according to the present invention comprises a monomer-containing kit component containing at least a (meth)acrylate monomer among titanium dioxide particles, a (meth)acrylate polymer, the (meth)acrylate monomer and a polymerization initiator, and a polymerization initiator-containing kit component containing at least the polymerization initiator.

In the bone cement composition kit according to the present invention, the polymerization initiator-containing kit component may preferably contain the titanium dioxide particles and (meth)acrylate polymer together with the polymerization initiator.

A bone cement formed material according to the present invention comprises titanium dioxide particles having a median diameter of 0.5 to 7.0 μm as measured by a laser diffraction/scattering type particle size distribution analyzer and a BET specific surface area of 0.5 to 7.0 $m^2/g$ as measured by a nitrogen adsorption method, and a base component comprising a (meth)acrylate polymer, wherein the content of the titanium dioxide particles is 5 to 50% by mass.

In the bone cement formed material according to the present invention, the median diameter and BET specific surface area of the titanium dioxide particles may be preferably 1.5 to 7.0 μm and 0.5 to 5.0 $m^2/g$, respectively.

In the bone cement formed material according to the present invention, the titanium dioxide particles may preferably have the following characteristics:
(1) the particles are rutile-type titanium dioxide particles;
(2) the particles are spherical;
(3) the particles are those subjected to an acid-washing treatment; and
(4) the particles are those produced by going through the steps of subjecting a slurry of titanic acid to a spray drying treatment, thereby obtaining dried granules, and subjecting the dried granules to a calcinating treatment.

The bone cement formed material according to the present invention may preferably have flexural strength of at least 70 MPa as measured according to the measuring method ISO 5833 prescribed by ISO standards.

The bone cement formed material according to the present invention may be used as an artificial bone.

A production method of a bone cement formed material according to the present invention comprises going through a polymerization step of polymerizing a (meth)acrylate monomer with a polymerization initiator in the presence of titanium dioxide particles having a median diameter of 0.5 to 7.0 µm as measured by a laser diffraction/scattering type particle size distribution analyzer and a BET specific surface area of 0.5 to 7.0 $m^2/g$ as measured by a nitrogen adsorption method and a (meth)acrylate polymer, thereby obtaining a bone cement formed material containing the titanium dioxide particles and a base component comprising the (meth)acrylate polymer, wherein the content of the titanium dioxide particles is 5 to 50% by mass based on the total mass of the formed material.

In the production method of the bone cement formed material according to the present invention, the polymerization initiator may be preferably benzoyl peroxide.

In the production method of the bone cement formed material according to the present invention, a polymerization accelerator may be preferably used in the polymerization step.

In the production method of the bone cement formed material according to the present invention, the amount of the (meth)acrylate polymer used in the polymerization step may be preferably 30 to 80% by mass based on the total mass of the amount of the (meth)acrylate polymer used and the amount of the (meth)acrylate monomer used in the polymerization step.

In the production method of the bone cement formed material according to the present invention, the formed material may be preferably formed in the polymerization step.

Advantageous Effects of the Invention

According to the bone cement composition of the present invention, titanium dioxide particles are contained therein, so that the apatite-forming ability under an environment of a body fluid that is possessed by the titanium dioxide particles themselves is manifested, and good flexural strength according to use applications in points of the size, form and content of the titanium dioxide particles is exhibited. Therefore, in a hardened material formed by polymerizing and hardening the (meth)acrylate monomer, high mechanical strength practically required can be achieved together with bioactivity.

According to the bone cement composition kit of the present invention, a bone cement composition can be obtained by subjecting the kit components to a simple mixing treatment, so that a hardened material or formed material of the bone cement composition can be easily produced. In addition, the (meth)acrylate monomer and the polymerization initiator are provided as separate kit components, so that the (meth)acrylate monomer can be prevented from being polymerized in a state stored or shipped before application.

According to the bone cement formed material of the present invention, titanium dioxide particles are contained therein, so that the apatite-forming ability under an environment of a body fluid that is possessed by the titanium dioxide particles themselves is manifested, and good flexural strength according to use applications in points of the size, form and content of the titanium dioxide particles is exhibited. Therefore, so high mechanical strength practically required can be achieved together with bioactivity.

According to the production method of the bone cement formed material of the present invention, a polymerization reaction of the (meth)acrylate monomer for forming the base component in the bone cement formed material to be formed is conducted in the presence of the specific titanium dioxide particles together with the (meth)acrylate polymer, whereby the formed material comprising the resulting hardened material comes to contain the specific titanium dioxide particles in the specific proportion. Therefore, the bone cement formed material having high mechanical strength together with bioactivity can be easily obtained.

BRIEF DESCRIPTION OF THE DRAWINGS

[FIG. 1] diagrammatically illustrates results of Example 12 and Comparative Example 4.

MODE FOR CARRYING OUT THE INVENTION

The present invention will hereinafter be described in detail.
<Bone Cement Composition>

The bone cement composition according to the present invention contains, as essential components, titanium dioxide particles having a median diameter of 0.5 to 7.0 µm as measured by a laser diffraction/scattering type particle size distribution analyzer and a BET specific surface area of 0.5 to 7.0 $m^2/g$ as measured by a nitrogen adsorption method, and a base-forming component comprising a (meth)acrylate polymer and a (meth)acrylate monomer, and the content of the titanium dioxide particles is 5 to 50% by mass, more preferably 5 to 30% by mass based on the total mass of the composition.

The bone cement composition according to the present invention is such that the (meth)acrylate monomer that is a polymerizable monomer of the base-forming component is polymerized, whereby the viscosity of the composition is gradually increased, and the composition becomes pasty and finally hardened to form a hardened material.
(Titanium Dioxide Particles)

The titanium dioxide particles that are an essential component of the bone cement composition according to the present invention have the specific median diameter and BET specific surface area and do not have a porous structure on the surface thereof when observed through an electron microscope. Thus, the particles are particles having a dense structure whose BET specific surface area is relatively small. The titanium dioxide particles make up a filler.

The titanium dioxide particles making up the bone cement composition according to the present invention are required to have a median diameter of 0.5 or more and 7.0 µm or less as measured by a laser diffraction/scattering type particle size distribution analyzer. The median diameter is preferably 1.5 to 7.0 µm, more preferably 2.0 to 7.0 µm, particularly preferably 2.0 to 6.5 µm.

Here, for example, a particle size distribution measuring instrument "LA-950" (manufactured by HORIBA, Ltd.) may be specifically used as "the laser diffraction/scattering type particle size distribution analyzer".

If the median diameter of the titanium dioxide particles is too small, sufficient mechanical strength (for example, flexural strength) practically required of a hardened material formed by polymerizing the (meth)-acrylate monomer is not achieved.

If the median diameter of the titanium dioxide particles is too large on the other hand, the mechanical strength (for example, flexural strength) of the hardened material formed by polymerizing the (meth)acrylate monomer becomes too great, so that such evils that a fracture caused by a great difference in mechanical strength between this hardened material and a bone of a site to be applied is easy to occur come to occur.

The titanium dioxide particles are also required to have a BET specific surface area of $0.5\ m^2/g$ or more and $7.0\ m^2/g$ or less as measured by a nitrogen adsorption method. The BET specific surface area is preferably $0.5$ to $5.0\ m^2/g$, more preferably $0.5$ to $4.0\ m^2/g$, particularly preferably $0.5$ to $3.0\ m^2/g$.

Here, for example, a BET specific surface area measuring instrument "MONOSORB" (manufactured by YUASA-IONICS Inc.) may be used in the measurement of the BET specific surface area by the nitrogen adsorption method.

If the BET specific surface area of the titanium dioxide particles is too small, the median diameter thereof becomes large. As a result, the mechanical strength (for example, flexural strength) of the hardened material formed by polymerizing the (meth)acrylate mer becomes too great, so that such evils that a fracture caused by a great difference in mechanical strength between this hardened material and a bone of a site to be applied is easy to occur come to occur.

If the BET specific surface area of the titanium dioxide particles is too large on the other hand, the mechanical strength (for example, flexural strength) practically required of the hardened material formed by polymerizing the (meth) acrylate monomer is not achieved, which is attributable to the fact that the median diameter of the titanium dioxide becomes too small or the titanium dioxide particles become an aggregated state or porous state.

The titanium dioxide particles making up the bone cement composition according to the present invention are preferably those having a median diameter of $1.5$ to $7.0\ \mu m$ and a BET specific surface area of $0.5$ to $5.0\ m^2/g$, more preferably those having a median diameter of $1.5$ to $7.0\ \mu m$ and a BET specific surface area of $0.5$ to $4.0\ m^2/g$, still more preferably those having a median diameter of $2.0$ to $7.0\ \mu m$ and a BET specific surface area of $0.5$ to $4.0\ m^2/g$, particularly preferably those having a median diameter of $2.0$ to $6.5\ \mu m$ and a BET specific surface area of $0.5$ to $3.0\ m^2/g$.

Here, when the titanium dioxide particles in the bone cement composition according to the present invention have a median diameter of $1.5$ to $7.0\ \mu m$ and a BET specific surface area of $0.5$ to $5.0\ m^2/g$, the sufficient mechanical strength (for example, flexural strength) practically required of the hardened material formed by polymerizing the (meth)acrylate monomer, specifically, such strength that flexural strength measured according to the measuring method based on ISO 5833 is at least 60 MPa, can be more surely achieved. In addition, when the titanium dioxide particles have a median diameter of $2.0$ to $6.5\ \mu m$ and a BET specific surface area of $0.5$ to $3.0\ m^2/g$ in particular, still higher mechanical strength (for example, flexural strength), specifically, such strength that flexural strength measured according to the measuring method based on ISO 5833 is at least 70 MPa, can be given to the hardened material formed by polymerizing the (meth) acrylate monomer.

As the titanium dioxide particles making up the bone cement composition according to the present invention, may be used those whose particle form is granular or indeterminate, which are obtained by an ordinary industrial production process, or those having various particle forms publicly known, such as plate, flake, needle, rod, fiber and column forms. However, those having a granular particle form are preferred, and preferable specific examples of the granular form include spherical forms such as true sphere and hemisphere.

The shape of the titanium dioxide particles is made spherical, whereby high flowability is imparted to such particles, and consequently uniform dispersibility in the composition and good filling ability are imparted thereto. As a result, the titanium dioxide particles come to be dispersed in a state high in uniformity in the hardened material and formed material formed from this composition, so that it is expected to prevent the titanium dioxide particles from separating from the hardened material and formed material.

In addition, in the bone cement composition according to the present invention, all the titanium dioxide particles making up the composition preferably have the same form.

Further, the titanium dioxide particles making up the bone cement composition according to the present invention may have any crystal structure of rutile-type, anatase-type and brookite-type and may be amorphous. However, rutile-type titanium dioxide particles are preferred because higher apatite-forming ability (bioactivity) is achieved.

Furthermore, the titanium dioxide particles preferably have hydrophilicity at the surfaces thereof within limits not impairing the affinity for the (meth)acrylate polymer because still higher apatite-forming ability (bioactivity) is achieved.

Examples of a method for imparting still higher hydrophilicity to the surfaces of the titanium dioxide particles include an acid-washing treatment which will be described subsequently.

Furthermore, the titanium dioxide particles preferably contain little impurities from the viewpoints of safety in a living body, to which the composition is applied, and preventing a prosthesis from being adversely affected. Specifically, the purity of the titanium dioxide is preferably at least 99% by mass, more preferably at least 99.5% by mass. On the other hand, the titanium dioxide particles may be subjected to a coating treatment with a small amount of an organic substance such as a silane coupling agent or an inorganic substance such as silica or alumina within limits not impairing the bioactivity and mechanical strength in the composition before use from the viewpoint of the affinity for the (meth) acrylate polymer.

The titanium dioxide particles having such a structure can be produced according to an ordinary method. However, the particles are most preferably produced according to the following method.

Specific examples of an optimum method for producing the titanium dioxide particles used in the bone cement composition according to the present invention include a method of obtaining titanium dioxide particles by going through the steps of using, for example, titanic acid as a raw material, subjecting a slurry of titanic acid as the raw material to a spray drying treatment after subjected to a wet grinding treatment, as needed, thereby obtain dried granules, and subjecting the dried granules to a calcinating treatment.

According to this method, the median diameter and BET specific surface area of the resulting titanium dioxide particles can be simply adjusted to respective desired ranges.

As titanic acid as the raw material of the titanium dioxide particles, may be specifically used orthotitanic acid and metatitanic acid.

Here, orthotitanic acid is a compound obtained by neutralizing an aqueous solution of a titanium compound such as titanium tetrachloride or titanyl sulfate with an alkali in the presence of a seed as needed, also called "titanium hydroxide" and represented by a rational formula of "$Ti(OH)_4$" or "$TiO_2.2H_2O$". Since this orthotitanic acid is amorphous, crystal dislocation is made even at a low heating temperature (calcinating temperature) in the calcinating treatment in such a manner that the resulting titanium dioxide particles have a rutile-type crystal structure. Thus, this acid is preferably used as the raw material.

Metatitanic acid is a compound obtained by thermally hydrolyzing a titanium compound such as titanyl sulfate in an aqueous solution thereof in the presence of a seed as needed, represented by a rational formula of "$TiO(OH)_2$" or "$TiO_2.H_2O$" and having an anatase-type crystal structure.

This titanic acid as the raw material is suspended in a solvent such as, for example, water, thereby preparing a slurry.

The wet grinding treatment, spray drying treatment and calcinating treatment to which the resultant titanic acid slurry is subjected will now be described below in detail.

(1) Wet Grinding Treatment

In this wet grinding treatment, the titanic acid slurry as the raw material is subjected to a grinding treatment, thereby grinding titanic acid in the slurry to obtain a ground titanic acid dispersion in a state that this ground titanic acid has been dispersed in a solvent.

This wet grinding treatment is a preferable treatment because titanic acid in the slurry is dispersed, whereby the median diameter of titanium dioxide particles obtained by going through the spray drying treatment and calcinating treatment of subsequent steps can be adjusted so as to become small.

As a grinding system in this wet grinding treatment, may be used a system that the slurry is caused to pass through an interstice of a rotating circular grindstone by, for example, a colloid mill to apply frictional force and shear force to the slurry to conduct grinding, or a system that the slurry is filled into a cylinder, into which a stirrer has been inserted, together with a spherical medium of rigid beads (for example, hard glass or ceramic) and mixed by, for example, a ball mill, Dyno mill or sand grinder to conduct grinding by high-speed stirring, mechanical impact by vibration, shear, friction and the like. Another grinding system by a pressure emulsifier type device, high-speed stirring device or the like may also be used.

A rutile dislocation-accelerating seed is preferably mixed in the titanic acid slurry or the ground titanic acid dispersion obtained by the wet grinding treatment.

When the rutile dislocation-accelerating seed is mixed as described above, crystal dislocation for causing the resulting titanium dioxide particles to have a rutile-type crystal structure is easy to occur in the calcinating treatment.

Here, "the rutile dislocation-accelerating seed" is a minute crystal nucleus having a rutile-type crystal structure and serves to accelerate rutile dislocation of titanic acid.

As the rutile dislocation-accelerating seed, may be specifically used, for example, a seed added upon hydrolysis of titanyl sulfate that is a raw material in a method for producing a rutile-type titanium dioxide white pigment by a sulfate process publicly known heretofore.

The amount of the rutile dislocation-accelerating seed mixed may be suitably set. However, the amount is preferably such that a mass ratio (mass of titanium dioxide in titanic acid/mass of titanium dioxide in the rutile dislocation-accelerating seed) to titanium dioxide present in the titanic acid slurry or ground titanic acid dispersion falls within a range of 90/10 to 99/1 because the rutile dislocation can be sufficiently caused.

For example, an ordinary mixing device such as a stirring and mixing machine or mixer may be used in the method for mixing the rutile dislocation-accelerating seed. The mixing of this rutile dislocation-accelerating seed may be conducted before or after the wet grinding treatment, or upon conducting the wet grinding treatment, i.e., at the same time as the wet grinding treatment.

(2) Spray Drying Treatment

In this spray drying treatment, a spray drying device is used to atomize and eject the titanic acid slurry or the ground titanic acid dispersion obtained by the wet grinding treatment conducted as needed as fine misty droplets from a nozzle of the spray drying device into hot air to dry it, thereby obtaining dry granules whose particle form is spherical.

An ordinary spray drying machine such as an ordinary spray dryer may be used as the spray drying device, and a spray system may be suitably selected from, for example, a disc system, a pressure nozzle system, a two-fluid nozzle system and a four-fluid nozzle system according to the properties of the titanic acid slurry or ground titanic acid dispersion, the capacity of the spray drying machine, etc.

The drying conditions (spray drying temperature) of the misty droplets are preferably 150 to 250° C. in intake air temperature and 60 to 120° C. in exhaust air temperature.

In such a spray drying treatment, the median diameter and BET specific surface area of the resulting dry granules can be controlled by, for example, adjusting a titanium dioxide concentration in the titanic acid slurry or ground titanic acid dispersion, adjusting a rotating speed of a disc when the disk system is selected as the spray system of the spray drying machine, or adjusting a spray pressure when the pressure nozzle system, two-fluid nozzle system or four-fluid nozzle system is selected as the spray system of the spray drying machine, thereby controlling the size of sprayed droplets.

In addition, the resulting dry granules can be provided as particles having the same spherical form depending on the spray drying treatment.

(3) Calcinating Treatment

In this calcinating treatment, the dry granules obtained by the spray drying treatment is subjected to a calcinating treatment under higher temperature conditions (specifically, higher than 250° C.) than the spray drying temperature in the spray drying treatment, thereby obtaining calcined particles composed of titanium dioxide.

According to this calcinating treatment, the crystal structure and hardness of the resulting calcined particles can be adjusted together with the median diameter and BET specific surface area of the calcined particles.

With respect to the calcinating conditions of the calcinating treatment, the calcinating temperature is preferably 500 to 1,200° C., more preferably 700 to 1,000° C., particularly preferably 800 to 950° C.

If the calcinating temperature is lower than 500° C., there is a possibility that the crystal dislocation conducted in order for the resulting titanium oxide particles to have a rutile-type crystal structure may be hard to proceed. If the calcinating temperature exceeds 1,200° C. on the other hand, the hardness of the resulting titanium dioxide particles becomes high, so that there is a possibility that abrasion by the titanium dioxide particles may occur on a bone or prosthesis at an application site of the composition.

The calcinating time may be suitable set. However, the time is specifically set to 30 minutes to 10 hours, whereby a sufficient effect by the calcinating, specifically, an effect to accelerate phase dislocation into a rutile type, can be achieved on the calcined particles formed.

No particular limitation is imposed on a calcinating atmosphere. However, an atmosphere, in which oxygen is present, such as the air, is preferred from the economical point of view.

In addition, the calcinating treatment may be such that a first calcinating treatment is conducted at a calcinating temperature of 500 to 800° C., and a second calcinating treatment is then conducted at a calcinating temperature of 800 to 1,200° C. for the purpose of evenly applying a calcinating load.

The calcined particles formed by going through the wet grinding treatment, spray drying treatment and calcinating treatment in this manner may be used as a component of the bone cement composition according to the present invention, i.e., the titanium dioxide particles making up the bone cement composition according to the present invention, as they are. However, the calcined particles obtained by the calcinating treatment are preferably subjected to an acid-washing treatment, as needed, for the purpose of imparting still higher hydrophilicity to the surfaces of the particles to achieve still higher apatite-forming ability (bioactivity).

(4) Acid-Washing Treatment

The acid-washing treatment may be conducted by, for example, preparing a slurry of the calcined particles, mixing this slurry with an acid and stirring the resultant mixture at room temperature or under heating. Titanium dioxide particles can be obtained by going through a solid-liquid separation treatment, a washing treatment and a drying treatment, and a cracking treatment conducted as needed after this acid-washing treatment.

Examples of usable acids include inorganic acids such as hydrochloric acid, sulfuric acid, nitric acid and hydrofluoric acid, and organic acids such as acetic acid, citric acid and oxalic acid. The concentration of the acid in the mixture of the slurry and the acid is, for example, 0.01 to 10 mol/L.

When the acid-washing treatment is conducted under heating, the heating is preferably conducted under conditions that the temperature of the mixture of the slurry and the acid is controlled to 30 to 105° C.

This acid-washing treatment is a treatment conducted for imparting still higher hydrophilicity to the surfaces of the titanium dioxide particles as needed and may also be applied to titanium dioxide particles produced by any other process in addition to the calcined particles.

In the course of the production of the titanium dioxide particles, as needed, the calcined particles may be subjected to other steps than such an acid-washing treatment, such as a dry grinding treatment using, for example, a centrifugal grinder or a wet grinding treatment using, for example, a ball mill, Dyno mill or sand grinder for the purpose of deflocculating (cracking) aggregates contained in the calcined particles obtained by the calcinating treatment, a wet classifying treatment by, for example, a stationary method for the purpose of screening out particles having a desired median diameter, and mixing of titanium dioxide particles different in median diameter and/or BET specific surface area from each other.

The content of the titanium dioxide particles making up the bone cement composition according to the present invention is required to be 5% by mass or more and 50% by mass or less based on the total mass of the composition. The content is preferably 5 to 40% by mass, more preferably 5 to 30% by mass, still more preferably 10 to 30% by mass, yet still more preferably 10 to 25% by mass, particularly preferably 15 to 20% by mass.

If the content of the titanium dioxide particles is too low, the sufficient bioactivity cannot be achieved.

If the content of the titanium dioxide particles is too high on the other hand, the mechanical strength (for example, flexural strength) practically required of the hardened material formed by polymerizing the (meth)acrylate monomer cannot be achieved.

Here, the content of the titanium dioxide particles in relation with the (meth)acrylate polymer, i.e., a proportion of the content of the titanium dioxide particles to the total compounding amount (total content) of the titanium dioxide particles and the (meth)acrylate polymer, is preferably 6 to 77% by mass, more preferably 6 to 46% by mass, still more preferably 13 to 46% by mass, yet still more preferably 13 to 38% by mass, particularly preferably 20 to 29% by mass.

((Meth)Acrylate Polymer)

The (meth)acrylate polymer that is an essential component of the bone cement composition according to the present invention is that making up a base-forming component together with a (meth)acrylate monomer which will be described subsequently.

The (meth)acrylate polymer is obtained by polymerizing (meth)acrylate monomer as a polymerizable monomer. Specific examples thereof include (A) polyalkyl methacrylates such as polymethyl methacrylate (PMMA), polyethyl methacrylate (PEMA) and polybutyl methacrylate (PBMA) that are polymers of alkyl methacrylate monomers such as methyl methacrylate (MMA), ethyl methacrylate (EMA) and butyl methacrylate, (B) copolymers obtained by copolymerizing methyl methacrylate with at least one monomer selected from the group consisting of styrene, ethyl methacrylate and methyl acrylate, and (C) polymers of dimethacrylate monomers such as bisphenol A diglycidyl dimethacrylate (Bis-GMA), 2,2-bis[4-(3-methacryloxy-2-hydroxypropoxy)-phenyl]propane, 2,2-bis(4-methacryloxyethoxyphenyl)-propane (Bis-MEPP), triethylene glycol dimethacrylate (TEGDMA), diethylene glycol dimethacrylate (DEGDMA) and ethylene glycol dimethacrylate (EGDMA).

The (meth)acrylate polymer making up the base-forming component of the bone cement composition according to the present invention is preferably that obtained by polymerizing the same polymerizable monomer as the (meth)acrylate monomer making up the base-forming component. Specifically, polymethyl methacrylate (PMMA) or a copolymer obtained by using methyl methacrylate as a polymerizable monomer is preferred from the relation with the (meth)acrylate monomer making up the base-forming component, and polymethyl methacrylate (PMMA) or a methyl methacrylate-styrene copolymer is particularly preferred.

As the (meth)acrylate polymer, is preferably used a powdered polymer having a weight-average molecular weight of preferably at least 100,000, more preferably 130,000 to 170,000.

In the powdered (meth)acrylate polymer, the particle diameter (average particle diameter) thereof is preferably 10 to 60 µm, more preferably 20 to 60 µm, still more preferably 30 to 50 µm, particularly preferably 35 to 45 µm.

Here, the average particle diameter of the (meth)acrylate polymer is a median diameter measured by a laser diffraction/scattering type particle size distribution analyzer. As the laser diffraction/scattering type particle size distribution analyzer, may be specifically used, for example, a particle size distribution measuring instrument "Microtrac" (manufactured by NIKKISO CO., LTD.).

The powdered (meth)acrylate polymer preferably has a spherical particle form.

When the shape of the (meth)acrylate polymer is made spherical, whereby high flowability is imparted to such a polymer, and consequently uniform dispersibility in the composition is imparted thereto.

The content of the (meth)acrylate polymer is preferably 30 to 80% by mass, more preferably 50 to 75% by mass, still more preferably 53 to 72% by mass, particularly preferably 59 to 72% by mass based on the total mass of the base-forming component.

If the content of the (meth)acrylate polymer is too low, the content of the (meth)acrylate monomer making up the base-forming component becomes too high, so that there is a possibility that it may take a long time to obtain the hardened material formed by polymerizing the (meth)acrylate monomer.

If the content of the (meth)acrylate polymer is too high on the other hand, there is a possibility that it may be impossible to contain other essential components in respective desired proportions or to contain optional components in respective necessary amounts.

((Meth)Acrylate Monomer)

The (meth)acrylate monomer that is an essential component of the bone cement composition according to the present invention is that making up the base-forming component together with the above-described (meth)acrylate polymer. This (meth)acrylate monomer that is a polymerizable monomer is polymerized, whereby the bone cement composition is hardened. As a result, the hardened material is obtained.

Specific examples of the (meth)acrylate monomer include those mentioned as the polymerizable monomers for obtaining the (meth)acrylate polymer making up the base-forming component, such as the alkyl methacrylate monomers and dimethacrylate monomers.

Preferable specific examples of the (meth)acrylate monomer include methyl methacrylate (MMA).

The content of the (meth)acrylate monomer is preferably 19 to 35% by mass, more preferably 25 to 35% by mass based on the total mass of the composition.

In addition to the titanium dioxide particles and the base-forming component comprising the (meth)acrylate monomer and the (meth)acrylate polymer that are essential components, the bone cement composition according to the present invention preferably comprises a polymerization initiator for the purpose of causing a polymerization reaction of the (meth)acrylate monomer to more rapidly start and proceed, and also preferably comprises a polymerization accelerator together with the polymerization initiator for the purpose of causing the polymerization reaction of the (meth)acrylate monomer to more rapidly proceed.

As the polymerization initiator, may be used, for example, benzoyl peroxide, tert-butyl peroxide, lauroyl peroxide or azobisisobutyronitrile.

Among these, benzoyl peroxide is preferably used because the polymerization reaction of the (meth)acrylate monomer can be caused to rapidly start, and this reaction is easy to be sustained.

The content of the polymerization initiator is preferably 1.0 to 10 parts by mass, more preferably 3 to 8 parts by mass per 100 parts by mass of the (meth)acrylate monomer.

If the content of the polymerization initiator is too low, there is a possibility that the polymerization reaction of the (meth)acrylate monomer may be hard to proceed. If the content of the polymerization initiator is too high on the other hand, the polymerization initiator is liable to remain in the hardened material of the bone cement composition, which is formed by polymerizing the (meth)acrylate monomer.

As the polymerization accelerator, may be used, for example, N,N-dimethyl-p-toluidine or 2,4,6-tris-(dimethylaminomethyl)phenol.

Among these, N,N-dimethyl-p-toluidine is preferably used because the polymerization reaction of the (meth)acrylate monomer can be caused to rapidly proceed.

The content of the polymerization accelerator is preferably 0.1 to 5 parts by mass, more preferably 0.3 to 3 parts by mass per 100 parts by mass of the (meth)acrylate monomer.

If the content of the polymerization accelerator is too low, there is a possibility that the polymerization reaction of the (meth)acrylate monomer may be hard to proceed. If the content of the polymerization accelerator is too high on the other hand, the polymerization accelerator is liable to remain in the hardened material of the bone cement composition, which is formed by polymerizing the (meth)acrylate monomer.

In the bone cement composition according to the present invention, any other inorganic substance than titanium dioxide, such as, for example, calcium phosphate (hydroxyapatite, tricalcium phosphate), barium sulfate, silicon oxide (silica), aluminum oxide (alumina) or zirconium oxide (zirconia), may be used as a filler together with the titanium dioxide particles that are an essential component of the bone cement composition and have the specific median diameter and BET specific surface area. In other words, in the bone cement composition according to the present invention, the titanium dioxide particles may be used, as the filler, either singly or in combination with one or more substances suitably selected from the other inorganic substances than titanium dioxide.

In addition, the bone cement composition according to the present invention may contain for example, pigments, antibiotic substances, bone growth factors and other pharmaceutically allowable optional components in addition to the polymerization initiator, polymerization accelerator and filler.

The bone cement composition of such constitution as described above according to the present invention contains the titanium dioxide particles having the specific median diameter and BET specific surface area together with the base-forming component comprising the (meth)acrylate polymer and the (meth)acrylate monomer, in the specific content. Therefore the apatite-forming ability under an environment of a body fluid that is possessed by the titanium dioxide particles themselves is manifested, and good flexural strength according to use applications in points of the size, form and content of the titanium dioxide particles is exhibited, and so in the hardened material formed by polymerizing and hardening the (meth)acrylate monomer, high mechanical strength practically required, specifically, such strength that flexural strength measured according to the measuring method based on ISO 5833 is at least 60 MPa, can be achieved together with bioactivity.

Accordingly, the bone cement composition according to the present invention can be used over a long period of time without any evil.

Since the bone cement composition according to the present invention has high mechanical strength together with high bioactivity, the composition can be suitably used as a prosthetic material for a defective part of a bone, an adhesive for fixing a metallic prosthesis such as a hip joint prosthesis to its surrounding bones or a fixing agent for prostheses and besides, can also be used as an artificial bone-forming material for forming an artificial bone.

In addition, the bone cement composition according to the present invention can also be applied in vivo, i.e., can be hardened by polymerizing the (meth)acrylate monomer in vivo. Specifically, the bone cement composition according to the present invention can be kneaded, introduced into a living body by a proper method and applied to a necessary application site such as, for example, a defective part of a bone, an adhesion part between a prosthesis and a bone or a fixing part of a prosthesis, thereby using it as a prosthetic material, adhesive or fixing agent.

Here, specific examples of a case where the bone cement composition according to the present invention is applied in vitro include an application as an artificial bone-forming material by, for example, embedding, for example, an artificial bone or artificial skull formed by hardening the composition in vitro in a living body.

Such a bone cement composition according to the present invention can be produced by mixing the titanium dioxide particles and the base-forming component comprising the (meth)acrylate polymer and the (meth)acrylate monomer, which are essential components, and other optional components. The composition may also be prepared as needed by, for example, containing the individual components in separate storage members in advance to store them as a kit from the viewpoint of simplicity and convenience of its production.

<Bone Cement Composition Kit>

The bone cement composition kit according to the present invention is the bone cement composition according to the present invention, which contains a polymerization initiator, and a bone cement composition kit for simply obtaining a hardened material and a formed material of the bone cement composition according to the present invention.

This bone cement composition kit according to the present invention comprises a monomer-containing kit component containing at least a (meth)acrylate monomer among titanium dioxide particles, a (meth)acrylate polymer, the (meth)acrylate monomer and a polymerization initiator, and a polymerization initiator-containing kit component containing at least the polymerization initiator.

Such a bone cement composition kit according to the present invention only requires to provide the (meth)acrylate monomer and the polymerization initiator as separate kit components from the viewpoint of preventing the (meth)acrylate monomer from undergoing a polymerization reaction before application. For example, the individual components may be provided as separate kit components. However, the kit is preferably composed of two kit components of a monomer-containing kit component and a polymerization initiator-containing kit component from the viewpoints of convenience of carrying the bone cement composition kit and simplicity of a polymerization reaction operation.

In the bone cement composition kit composed of the two kit components of the monomer-containing kit component and the polymerization initiator-containing kit component, the titanium dioxide particles, (meth)acrylate polymer and polymerization initiator among the essential components are generally solid, and the (meth)acrylate monomer is generally liquid, so that it is preferable that only the (meth)acrylate monomer is contained in the monomer-containing kit component, and the (meth)acrylate polymer and titanium dioxide particles are contained in the polymerization initiator-containing kit component together with the polymerization initiator.

When a polymerization accelerator and/or another filler than the titanium dioxide particles, specifically, another inorganic substance (hereinafter also referred to as "filler-forming inorganic substance") than titanium dioxide are contained together with the titanium dioxide particles, (meth)acrylate polymer, (meth)acrylate monomer and polymerization initiator in the bone cement composition kit according to the present invention, these polymerization accelerator and/or filler-forming inorganic substance may be provided as separate kit components from the monomer-containing kit component and the polymerization initiator-containing kit component. However, these components are preferably contained in any one of these two kit components from the viewpoints of convenience of carrying the kit and simplicity of a polymerization reaction operation.

Specifically, the polymerization accelerator is generally in a liquid state and does not have reactivity to the (meth)acrylate monomer, so that the accelerator is preferably contained in the monomer-containing kit component of the two kit components. On the other hand, the filler-forming inorganic substance is generally in a solid state, so that the inorganic substance is preferably contained in the polymerization initiator-containing kit component of the two kit components.

As storage members for storing the kit components of the bone cement composition kit, any members may be used so far as they can store and carry the respective kit components. For example, glass, metal or plastic containers, or packaging members made of, for example, paper or plastics may be suitably selected for use.

According to such a bone cement composition kit of the present invention, a bone cement composition can be obtained by subjecting the kit components to a simple mixing treatment, so that a hardened material or formed material of the bone cement composition can be easily produced. In addition, the (meth)acrylate monomer and the polymerization initiator are provided as separate kit components, so that the (meth)acrylate monomer can be prevented from being polymerized in a state stored or shipped before application.

When the bone cement composition kid according to the present invention is composed of the two kit components of the monomer-containing kit component and the polymerization initiator-containing kit component, the total number of kit components is small, so that the convenience of carrying the bone cement composition kit and the simplicity of the polymerization reaction operation become far excellent.

<Bone Cement Formed Material>

The bone cement formed material according to the present invention comprises, as essential components, titanium dioxide particles having the specific median diameter and BET specific surface area, and a base component comprising a (meth)acrylate polymer, wherein the content of the titanium dioxide particles is 5 to 50% by mass, preferably 5 to 30% by mass based on the total mass of the formed material. The formed material is composed of a hardened material of the bone cement composition according to the present invention.

More specifically, the bone cement formed material according to the present invention is composed of a hardened material formed by using the bone cement composition according to the present invention as a material and polymerizing the (meth)acrylate monomer making up the base-forming component in the bone cement composition. The base component of the bone cement formed material comprises the (meth)acrylate polymer that is a base-forming component of the bone cement composition according to the present invention as a material, and a polymer formed by polymerizing the (meth)acrylate monomer that is a base-forming component likewise.

In the bone cement formed material according to the present invention, the content of the titanium dioxide particles is required to be 5% by mass or more and 50% by mass or less based on the total mass of the formed material like the bone cement composition according to the present invention that is a material. The content is preferably 5 to 40% by mass, more preferably 5 to 30% by mass, still more preferably 10 to 30% by mass, yet still more preferably 10 to 25% by mass, particularly preferably 15 to 20% by mass.

If the content of the titanium dioxide particles is too low, the sufficient bioactivity cannot be achieved.

If the content of the titanium dioxide particles is too high on the other hand, the mechanical strength (for example, flexural strength) practically required cannot be achieved.

In the bone cement formed material according to the present invention, the flexural strength measured according to the measuring method based on ISO standard, specifically, ISO 5833 is at least 60 MPa, preferably at least 65 MPa, more preferably at least 70 MPa, particularly preferably at least 75 MPa.

In the bone cement formed material according to the present invention, the flexural modulus measured according to the measuring method based on ISO 5833 is at least 1,800 MPa, and the average compressive strength measured according to the same method is at least 70 MPa.

According to such a bone cement formed material of the present invention, the specific titanium dioxide particles are contained in the specific proportion together with the base component comprising the (meth)acrylate polymer, so that the apatite-forming ability under an environment of a body fluid that is possessed by the titanium dioxide particles themselves is manifested, and good flexural strength according to use applications in points of the size, form and content of the titanium dioxide particles is exhibited, and so high mechanical strength practically required can be achieved together with bioactivity.

Since the bone cement formed material according to the present invention has high mechanical strength together with the bioactivity, the formed material can be suitably used as an artificial bone, and besides, can also be used as, for example, an artificial bone material for being embedded in a defective part of a bone.

<Production Method of Bone Cement Formed Material>

The production method of a bone cement formed material according to the present invention comprises going through a polymerization step of polymerizing a (meth)acrylate monomer with a polymerization initiator in the presence of titanium dioxide particles having the specific median diameter and BET specific surface area and a (meth)acrylate polymer, thereby obtaining a bone cement formed material containing the titanium dioxide particles and a base component comprising the (meth)acrylate polymer.

In short, the production method of the bone cement formed material according to the present invention comprises using the bone cement composition according to the present invention as a material and forming a hardened material formed by polymerizing the (meth)acrylate monomer making up the base-forming component in the bone cement composition, thereby obtaining the bone cement formed material according to the present invention.

Specifically, in the polymerization step in this production method of the bone cement formed material according to the present invention, the (meth)acrylate monomer is added into a container charged with the titanium dioxide particles, the (meth)acrylate polymer and the polymerization initiator, and the contents are kneaded to bring the (meth)acrylate monomer into contact with the polymerization initiator, thereby causing a polymerization reaction of the (meth)acrylate monomer to proceed to harden the (meth)acrylate monomer so as to form a hardened material as a bone cement formed material.

In this polymerization step, it is preferable that the kneaded product of the titanium dioxide particles, the (meth)acrylate polymer, the (meth)acrylate monomer and the polymerization initiator is put in a container having a desired shape and releasability and hardened and formed in that state, thereby forming a formed material so as to have a shape conforming to the shape of the container.

Specifically, for example, a mixture of the titanium dioxide particles, the (meth)acrylate polymer, the (meth)acrylate monomer and the polymerization initiator is kneaded in a closed container capable of degassing under vacuum, and this kneaded product is put in a container having a shape conforming to the shape of a bone cement formed material to be formed and releasability before being hardened, and left at rest and hardened in that state, thereby forming it to form a formed material having the desired shape, i.e., a bone cement formed material.

In this polymerization step, the conditions for forming the formed material vary according to the respective kinds and used amounts of the titanium dioxide particles, the (meth)acrylate polymer, the (meth)acrylate monomer and the polymerization initiator, the shape of the formed material to be formed, and the like. However, as the kneading conditions, the kneading time is 1 minute under, for example, a degassed atmosphere, and as the standing conditions, the standing time is at least 24 hours under, for example, an environment of 30° C. in temperature.

According to such a production method of the bone cement formed material of the present invention, the polymerization reaction of the (meth)acrylate monomer for forming the base component in the bone cement formed material to be formed is conducted in the presence of the specific titanium dioxide particles together with the (meth)acrylate polymer, whereby the formed material composed of the resulting hardened material comes to contain the specific titanium dioxide particles in the specific proportion, so that the bone cement formed material having high mechanical strength together with bioactivity can be easily obtained.

EXAMPLES

Examples of the present invention will hereinafter be specifically described. However, the present invention is not limited to these Examples.

Methods for measurements of the median diameters and BET specific surface areas of titanium dioxide particles, titanium dioxide concentrations, and the average particle diameters of (meth)acrylate polymers, which were conducted in the following Examples and Comparative Examples, are as follows.

(Measuring Method of Median Diameter of Titanium Dioxide Particles)

The median diameter was measured by a laser diffraction/scattering type particle size distribution analyzer, and the measurement was conducted by using a particle size distribution measuring instrument "LA-950" (manufactured by HORIBA, Ltd.) as the laser diffraction/scattering type particle size distribution analyzer.

More specifically, powder particles, the median diameter of which was to be measured, were added into 50 mL of a dispersion medium composed of an aqueous sodium hexametaphosphate solution having a concentration of 0.2% by mass, and the resultant mixture was stirred and mixed, thereby preparing a suspension. This suspension was poured from a sample inlet port into the particle size distribution measuring instrument "LA-950" (manufactured by HORIBA, Ltd.) and subjected to an ultrasonic treatment for 3 minutes, and the measurement was then started.
(Measuring Method of Bet Specific Surface Area of Titanium Dioxide Particles)

The BET specific surface area was measured by a nitrogen adsorption method, and the measurement was conducted by using a BET specific surface area measuring instrument "MONOSORB" (manufactured by YUASA-IONICS Inc.).

This BET specific surface area measuring instrument "MONOSORB" (manufactured by YUASA-IONICS Inc.) is suitable for the measurement by the BET single point method.
(Measuring Method of Titanium Dioxide Concentration)

The titanium dioxide concentration, specifically, the titanium dioxide concentrations in an orthotitanic acid slurry and a rutile dislocation-accelerating seed slurry were measured by taking each slurry in a crucible to dry it and then subjecting it to a calcinating treatment under conditions of 750° C. in temperature.
(Measuring Method of Average Particle Diameter of (Meth) Acrylate Polymer)

As the average particle diameter, a median diameter was measured by a laser diffraction/scattering type particle size distribution analyzer, and a particle size distribution measuring instrument "Microtrac" (manufactured by NIKKISO CO., LTD.) was used as the laser diffraction/scattering type particle size distribution analyzer.

More specifically, powder particles, the average particle diameter of which was to be measured, were added into 50 mL of a dispersion medium composed of Tween 20 (polyoxyethylene (20) sorbitan monolaurate) having a concentration of 0.2% by mass, and the resultant mixture was stirred and mixed and then subjected to an ultrasonic treatment for 1 minute, thereby preparing a suspension. This suspension was poured from a sample inlet port into the particle size distribution measuring instrument "Microtrac" (manufactured by NIKKISO CO., LTD.) and subjected to an ultrasonic treatment for 3 minutes, and the measurement was then started.

Preparation Example 1 of Titanium Dioxide Particles

Preparation of Titanic Acid Slurry

After an aqueous titanium tetrachloride solution was neutralized with aqueous ammonia, filtration and water washing were conducted, thereby obtaining orthotitanic acid in a wet cake state. Thereafter, the resultant orthotitanic acid in the wet cake state and pure water were charged into a mixer and sufficiently stirred and mixed, thereby obtaining an orthotitanic acid slurry. The median diameter of ortho titanic acid particles making up this orthotitanic acid slurry was measured and found to be 6.8 μm.
(Wet Grinding Process)

A Dyno mill "DYNO-MILL" (manufactured by SHIN-MARU ENTERPRISES CORPORATION) was used to charge 480 mL of titania beads (product of Toyama Ceramics Co., Ltd.) having an average particle diameter of 0.6 mm into the interior (volume: about 600 mL) of this Dyno mill body, and the above-obtained orthotitanic acid slurry was fed under conditions of a flow rate of 160 mL/min and treated in the Dyno mill by rotating a rotor blade provided in the interior of the mill body, thereby obtaining an orthotitanic acid slurry (hereinafter also referred to as "the grinding treatment-subjected titanic acid slurry (a)").

The concentration of titanium dioxide in this grinding treatment-subjected titanic acid slurry (a) was 9.15% by mass, and the median diameter of ortho titanic acid particles making up this grinding treatment-subjected titanic acid slurry (a) was measured and found to be 1.7 μm.

(Spray Drying Process)

A rutile dislocation-accelerating seed slurry having a titanium dioxide concentration of 16.08% by mass was first mixed with the grinding treatment-subjected titanic acid slurry (a) obtained in Wet grinding process in a proportion that a mass ratio (mass of titanium dioxide in titanic acid/mass of titanium dioxide in the rutile dislocation-accelerating seed) to titanium dioxide present in the grinding treatment-subjected titanic acid slurry (a) is 95/5, and the concentration of titanium dioxide in this mixture was adjusted to 1.5% by mass by adding pure water thereto, thereby preparing a mixed slurry. After the resultant mixed slurry was stirred and mixed by means of a domestic mixer, coarse particles were removed by a 400-mesh sieve, thereby obtaining a slurry for spray drying treatment (hereinafter also referred to as "the slurry (a) for spray drying treatment").

A spray drying machine "MDL-050C" (manufactured by Fujisaki Electric Co., Ltd.) was then used, and the slurry (a) for spray drying treatment was fed to this spray drying machine by a roller pump to conduct a spray drying treatment under conditions of a roller pump flow rate of 30 mL/min (set flow rate when pure water was fed), an intake air temperature of 200° C., an exhaust air temperature of 65 to 85° C. and an air flow rate of 80 L/min. In a powder collecting part provided in the spray drying machine and comprises a glass container and a bag filter, portions large in median diameter and portions small in median diameter of the dried granules obtained by this spray drying treatment were collected in the glass container and the bag filter, respectively.

Here, the portions collected in the glass container of the spray drying machine are called "cyclone product", and the portions collected in the bag filter are called "bag product" on the other hand.
(Calcinating Process)

Those collected as the cyclone product of the dried granules obtained in Spray drying process and having a median diameter of 1.9 μm were first put in a calcinating crucible to conduct a first calcinating treatment by means of an electric furnace "SK-3035F" (manufactured by MOTOYAMA CO., LTD.) under calcinating conditions of a calcinating temperature of 650° C. (heating rate: 10° C./min) and a calcinating time of 3 hours, and air cooling was then conducted. Thereafter, the air-cooled calcined product of the dried granules was subjected to a dry grinding treatment by means of a centrifugal grinder "ZM1" (manufactured by NIHONSEIKI KAISHA LTD.), in which a mesh having a screen diameter of 2 mm had been set, under conditions of a rotating speed of 12,000 rpm.

The calcined intermediate subjected to the dry grinding treatment was then put in a calcinating crucible to conduct a second calcinating treatment by means of the electric furnace "SK-3035F" (manufactured by MOTOYAMA CO., LTD.) under calcinating conditions of a calcinating temperature of 950° C. (heating rate: 10° C./min) and a calcinating time of 3 hours, and air cooling was then conducted. Thereafter, calcined particles, which were an air-cooled calcined product of the intermediate calcined product, were subjected to a dry grinding treatment by means of the centrifugal grinder "ZM1" (manufactured by NIHONSEIKI KAISHA LTD.), in which a mesh having a screen diameter of 2 mm had been set, under conditions of a rotating speed of 12,000 rpm, thereby obtaining calcined particles.
(Acid-Washing Process)

The calcined particles obtained in Calcinating process were added into 1N hydrochloric acid and stirred overnight at room temperature by means of a stirring motor, thereby conducting an acid-washing treatment. Thereafter, a supernatant was removed by decantation, the residue was filtered and washed with pure water by means of a Buchner funnel to confirm that the specific resistance of a filtrate is at least 10 kΩ.m. The thus-treated residue was then subjected to a drying treatment under conditions of a temperature of 110° C. by means of a constant-temperature drying machine and to a dry grinding treatment by means of the centrifugal grinder "ZM1" (manufactured by NIHONSEIKI KAISHA LTD.), in which a mesh having a screen diameter of 2 mm had been set, under conditions of a rotating speed of 12,000 rpm, thereby obtaining titanium dioxide particles (hereinafter also referred to as "titanium dioxide particles (A)").

The median diameter and BET specific surface area of the resultant titanium dioxide particles (A) were measured and found to be 2.3 μm and 2.02 m$^2$/g, respectively.

From a result of powder X-ray diffraction using a powder X-ray diffractometer "RINT 1200" (manufactured by Rigaku Corporation), it was confirmed that the titanium dioxide particles (A) are rutile-type titanium dioxide particles, and from a result of observation through an electron microscope, it was confirmed that the shape thereof is spherical.

Preparation Example 2 of Titanium Dioxide Particles

Titanium dioxide particles (hereinafter also referred to as "titanium dioxide particles (B)") were obtained in the same manner as in Preparation Example 1 of titanium dioxide particles except that an orthotitanic acid slurry (grinding treatment-subjected titanic acid slurry), the titanium dioxide concentration in the orthotitanic acid of which was 8.03% by mass, was obtained in Preparation of titanic acid slurry and Wet grinding process in Preparation Example 1 of titanium dioxide particles, a mixed slurry of the grinding treatment-subjected titanic acid slurry and the rutile dislocation-accelerating seed slurry was prepared so as to give a titanium dioxide concentration of 4.0% by mass in Spray drying process, thereby obtaining a slurry for spray drying treatment, this slurry for spray drying treatment was used to obtain dried granules having a median diameter of 3.4 μm and dried granules having a median diameter of 3.6 μm as separate cyclone products, the dried granules having a median diameter of 3.4 μm and the dried granules having a median diameter of 3.6 μm were individually subjected to the calcinating treatment in Calcinating process, thereby subjecting them to the dry grinding treatment to obtain two kinds of calcined particles, the thus-obtained two kinds of calcined particles were mixed and added into pure water to obtain a suspension, and a residue collected by a spontaneous sedimentation method after this suspension was filtered by means of a sieve having an opening of 10 μm was subjected to Acid-washing process.

The median diameter and BET specific surface area of the resultant titanium dioxide particles (B) were measured and found to be 2.9 μm and 1.90 m$^2$/g, respectively.

From a result of powder X-ray diffraction using the powder X-ray diffractometer "RINT 1200" (manufactured by Rigaku Corporation), it was confirmed that the titanium dioxide particles (B) are rutile-type titanium dioxide particles, and from a result of observation through the electron microscope, it was confirmed that the shape thereof is spherical.

Preparation Example 3 of Titanium Dioxide Particles

Titanium dioxide particles (hereinafter also referred to as "titanium dioxide particles (C)") were obtained in the same manner as in Preparation Example 1 of titanium dioxide particles except that an orthotitanic acid slurry, the titanium dioxide concentration in the orthotitanic acid of which was 9.22% by mass, was obtained in Preparation of titanic acid slurry in Preparation Example 1 of titanium dioxide particles, Wet grinding process was not conducted, a mixed slurry of the orthotitanic acid slurry and the rutile dislocation-accelerating seed slurry was prepared so as to give a titanium dioxide concentration of 7.0% by mass in Spray drying process, thereby obtaining a slurry for spray drying treatment, and dried granules having a median diameter of 6.0 μm were obtained as a cyclone product.

The median diameter and BET specific surface area of the resultant titanium dioxide particles (C) were measured and found to be 5.1 μm and 0.85 m$^2$/g, respectively.

From a result of powder X-ray diffraction using the powder X-ray diffractometer "RINT 1200" (manufactured by Rigaku Corporation), it was confirmed that the titanium dioxide particles (C) are rutile-type titanium dioxide particles, and from a result of observation through the electron microscope, it was confirmed that the shape thereof is spherical.

Preparation Example 4 of Titanium Dioxide Particles

Titanium dioxide particles (hereinafter also referred to as "titanium dioxide particles (D)") were obtained in the same manner as in Preparation Example 3 of titanium dioxide particles except that the air flow rate of the conditions of the spray drying treatment by the spray drying machine in Spray drying process in Preparation Example 3 of titanium dioxide particles was changed to 40 L/min, and dried granules having a median diameter of 7.4 μm were obtained as a cyclone product.

The median diameter and BET specific surface area of the resultant titanium dioxide particles (D) were measured and found to be 6.4 μl and 0.59 m$^2$/g, respectively.

From a result of powder X-ray diffraction using the powder X-ray diffractometer "RINT 1200" (manufactured by Rigaku Corporation), it was confirmed that the titanium dioxide particles (D) are rutile-type titanium dioxide particles, and from a result of observation through the electron microscope, it was confirmed that the shape thereof is spherical.

Preparation Example 5 of Titanium Dioxide Particles

Titanium dioxide particles (hereinafter also referred to as "titanium dioxide particles (E)") were obtained in the same manner as in Preparation Example 1 of titanium dioxide particles except that an orthotitanic acid slurry (grinding treatment-subjected titanic acid slurry), the titanium dioxide concentration in the orthotitanic acid of which was 9.44% by mass, was obtained in Preparation of titanic acid slurry and Wet grinding process in Preparation Example 1 of titanium dioxide particles, a mixed slurry of the grinding treatment-subjected titanic acid slurry and a rutile dislocation-accelerating seed slurry having a titanium dioxide concentration of 24.43% by mass was prepared so as to give a titanium dioxide concentration of 4.0% by mass in Spray drying process, thereby obtaining a slurry for spray drying treatment, the resultant bag product was used in Calcinating process, and the calcined particles obtained in Calcinating process were subjected to a wet treatment for 24 hours by means of a pot mill and then subjected to Acid-washing process.

The median diameter and BET specific surface area of the resultant titanium dioxide particles (E) were measured and found to be 1.2 μm and 3.40 m$^2$/g, respectively.

From a result of powder X-ray diffraction using the powder X-ray diffractometer "RINT 1200" (manufactured by Rigaku Corporation), it was confirmed that the titanium dioxide particles (E) are rutile-type titanium dioxide particles, and from a result of observation through the electron microscope, it was confirmed that the shape thereof is spherical.

Preparation Example 6 of Titanium Dioxide Particles

In this Preparation Example 6 of titanium dioxide particles, two kinds of particles different in median diameter were separately prepared, and titanium dioxide particles used in Preparation Example of formed material of bone cement composition were finally prepared by mixing the two kinds of particles thus prepared.

Preparation Example 6-1

Preparation Example of first Titanium Dioxide Particles

Titanium dioxide particles (hereinafter also referred to as "titanium dioxide particles (F-1)") having a median diameter of 1.1 μm were obtained in the same manner as in Preparation Example 1 of titanium dioxide particles except that an orthotitanic acid slurry (grinding treatment-subjected titanic acid slurry), the titanium dioxide concentration in the orthotitanic acid of which was 8.10% by mass, was obtained in Preparation of titanic acid slurry and Wet grinding process in Preparation Example 1 of titanium dioxide particles, a mixed slurry of the grinding treatment-subjected titanic acid slurry and a rutile dislocation-accelerating seed slurry having a titanium dioxide concentration of 17.20% by mass was prepared so as to give a titanium dioxide concentration of 4.0% by mass in Spray drying process, thereby obtaining a slurry for spray drying treatment, the flow rate conditions of the roller pump in the spray drying treatment were changed to 25 mL/min to obtain dried granules having a median diameter of 1.2 μm as a bag product, the resultant bag product was used in Calcinating process, the calcined particles obtained in Calcinating process were subjected to a wet treatment for 40 hours by means of a pot mill and then subjected to Acid-washing process, and the dry grinding treatment in Acid-washing process was conducted by means of a centrifugal grinder "ZM100" (manufactured by NIHONSEIKI KAISHA LTD.), in which a mesh having a screen diameter of 1.5 mm had been set, under conditions of a rotating speed of 14,000 rpm.

Preparation Example 6-2

Preparation Example of Second Titanium Dioxide Particles

Titanium dioxide particles (hereinafter also referred to as "titanium dioxide particles (F-2)") having a median diameter of 0.3 μm were obtained in the same manner as in Preparation Example 1 of titanium dioxide particles except that an orthotitanic acid slurry (grinding treatment-subjected titanic acid slurry), the titanium dioxide concentration in the orthotitanic acid of which was 8.10% by mass, was obtained in Preparation of titanic acid slurry and Wet grinding process in Preparation Example 1 of titanium dioxide particles, a mixed slurry of the grinding treatment-subjected titanic acid slurry and a rutile dislocation-accelerating seed slurry having a titanium dioxide concentration of 17.20% by mass, the titanium dioxide concentration in which was adjusted to 1.0% by mass, was filtered by means of a sieve having an opening of 5 μm in Spray drying process to obtain a slurry for spray drying treatment, the flow rate conditions of the roller pump in the spray drying treatment were changed to 20 mL/min to obtain dried granules having a median diameter of 1.0 μm as a bag product, the resultant bag product was used in Calcinating process, the calcinating temperature in the second calcinating treatment was changed to 850° C., the calcined particles obtained in Calcinating process were subjected to a wet treatment for 17 hours by means of a pot mill and then subjected to Acid-washing process, the filtration and washing with pure water in Acid-washing process were conducted by means of a membrane filter having a pore size of 0.45 μm, and the dry grinding treatment was conducted by means of a centrifugal grinder "ZM100" (manufactured by NIHONSEIKI KAISHA LTD.), in which a mesh having a screen diameter of 1.5 mm had been set, under conditions of a rotating speed of 14,000 rpm.

Thirty grams of the titanium dioxide particles (F-1) obtained in Preparation Example 6-1 and 19 g of the titanium dioxide particles (F-2) obtained in Preparation Example 6-2 were mixed, thereby obtaining titanium dioxide particles (hereinafter also referred to as "titanium dioxide particles (F)").

The median diameter and BET specific surface area of the resultant titanium dioxide particles (F) were measured and found to be 0.7 μm and 6.73 m$^2$/g, respectively.

From a result of powder X-ray diffraction using the powder X-ray diffractometer "RINT 1200" (manufactured by Rigaku Corporation), it was confirmed that the titanium dioxide particles (F) are rutile-type titanium dioxide particles, and from a result of observation through the electron microscope, it was confirmed that the shape thereof is spherical.

Preparation Example 1 of Comparative Titanium Dioxide Particles

Spray Drying Process

A rutile dislocation-accelerating seed slurry having a concentration of 2.0% by mass was first prepared with a rutile dislocation-accelerating seed and pure water. After the this slurry was stirred and mixed by means of a domestic mixer, coarse particles were removed by a 200-mesh sieve, thereby obtaining a slurry for spray drying treatment.

A spray drying machine "MDL-050C" (manufactured by Fujisaki Electric Co., Ltd.) was then used, and the above slurry for spray drying treatment was fed to this spray drying machine by a roller pump to conduct a spray drying treatment under conditions of a roller pump flow rate of 30 mL/min, an intake air temperature of 200° C., an exhaust air temperature of 70 to 90° C. and an air flow rate of 110 L/min. In a powder collecting part provided in the spray drying machine and comprises of a glass container and a bag filter, dried granules having a median diameter of 2.7 μm of the dried granules obtained by this spray drying treatment were collected in the glass container as a cyclone product.

(Calcinating Process)

The cyclone product (those having a median diameter of 2.7 μm) of the dried granules obtained in Spray drying process was put in a calcinating crucible to conduct a first calcinating treatment by means of an electric furnace "SS-2030PKP" (manufactured by MOTOYAMA CO., LTD.) under calcinating conditions of a calcinating temperature of 650° C. (heating rate: 10° C./min) and a calcinating time of 3 hours, and air cooling was then conducted. Thereafter, the air-cooled calcined product (intermediate calcined product) of the dried granules was stirred to conduct a second calcinating treatment again by means of the electric furnace "SS-2030PKP" (manufactured by MOTOYAMA CO., LTD.) under calcinating conditions of a calcinating temperature of 650° C. (heating rate: 10° C./min) and a calcinating time of 3 hours, and air cooling was then conducted. Thereafter, calcined particles, which were an air-cooled calcined product of the intermediate calcined product, were subjected to a dry grinding treatment by means of the centrifugal grinder "ZM100" (manufactured by NIHONSEIKI KAISHA LTD.) under conditions of a rotating speed of 14,000 rpm, thereby obtaining calcined particles.
(Acid-Washing Process)

The calcined particles obtained in Calcinating process were stirred by a domestic mixer and then added into hydrochloric acid to obtain a suspension. The pH of the suspension was adjusted to 8.5, coarse particles were removed by a sieve having an opening of 10 μm, and a process that a supernatant was removed by suction using a spontaneous sedimentation method was repeated twice, thereby removing minute particles. The residue was then added to pure water to obtain a suspension, sulfuric acid was added to the suspension in such a manner that the concentration thereof is 1 mol/L, the resultant mixture was left at rest overnight, thereby conducting an acid-washing treatment. Thereafter, a supernatant was removed, the residue was filtered and washed with pure water by means of a Buchner funnel, and the thus-treated residue was then subjected to a drying treatment by means of a constant-temperature drying machine and to a dry grinding treatment by means of the centrifugal grinder "ZM100" (manufactured by NIHONSEIKI KAISHA LTD.) under conditions of a rotating speed of 14,000 rpm, thereby obtaining titanium dioxide particles (hereinafter also referred to as "comparative titanium dioxide particles (G)").

The median diameter and BET specific surface area of the resultant comparative titanium dioxide particles (G) were measured and found to be 3.4 μm and 30.6 m$^2$/g, respectively.

Preparation Example 2 of Comparative Titanium Dioxide Particles

Preparation of Titanic Acid Slurry

After an aqueous titanium tetrachloride solution was neutralized with aqueous ammonia, filtration and water washing were conducted, thereby obtaining orthotitanic acid. Thereafter, the resultant orthotitanic acid and pure water were charged into a mixer and sufficiently stirred and mixed, thereby obtaining an orthotitanic acid slurry. The median diameter of ortho titanic acid particles making up this orthotitanic acid slurry was measured and found to be 6.9 μm.
(Wet Grinding Process)

A Dyno mill "DYNO-MILL" (manufactured by SHINMARU ENTERPRISES CORPORATION) was used to charge 480 mL of titania beads (product of Toyama Ceramics Co., Ltd.) having an average particle diameter of 0.6 mm into the interior (volume: about 600 mL) of this Dyno mill body, and the above-obtained orthotitanic acid slurry was fed under conditions of a flow rate of 160 mL/min and treated in the Dyno mill by rotating a rotor blade provided in the interior of the mill body, thereby obtaining an orthotitanic acid slurry (hereinafter also referred to as "the grinding treatment-subjected titanic acid slurry (h)".

The concentration of titanium dioxide in this grinding treatment-subjected titanic acid slurry (h) was 8.22% by mass, and the median diameter of ortho titanic acid particles making up this grinding treatment-subjected titanic acid slurry (h) was measured and found to be 1.7 μm.
(Spray Drying Process)

A rutile dislocation-accelerating seed slurry (titanium dioxide concentration: 24.40% by mass) was first mixed with the grinding treatment-subjected titanic acid slurry (h) obtained in Wet grinding process in a proportion that a mass ratio (mass of titanium dioxide in titanic acid/mass of titanium dioxide in the rutile dislocation-accelerating seed) to titanium dioxide present in the grinding treatment-subjected titanic acid slurry (h) is 5/95, and the concentration of titanium dioxide in this mixture was adjusted to 20% by mass by adding pure water thereto, thereby preparing a mixed slurry. After the resultant mixed slurry was stirred and mixed by means of a domestic mixer, coarse particles were removed by a 200-mesh sieve, thereby obtaining a slurry for spray drying treatment (hereinafter also referred to as "the slurry (h) for spray drying treatment").

A spray drying machine "MDL-050C" (manufactured by Fujisaki Electric Co., Ltd.) was then used, and the slurry (h) for spray drying treatment was fed to this spray drying machine by a roller pump to conduct a spray drying treatment under conditions of a roller pump flow rate of 40 mL/min, an intake air temperature of 210 to 220° C., an exhaust air temperature of 65 to 85° C. and an air flow rate of 60 L/min. In a powder collecting part provided in the spray drying machine and comprises a glass container and a bag filter, dried granules having a median diameter of 7.0 μm of the dried granules obtained by this spray drying treatment were collected in the glass container as a cyclone product.
(Calcinating Process)

The cyclone product (specifically, those having a median diameter of 7.0 μm) of the dried granules obtained in Spray drying process was put in a calcinating crucible to conduct a calcinating treatment by means of an electric furnace "SK-3035F" (manufactured by MOTOYAMA CO., LTD.) under calcinating conditions of a calcinating temperature of 650° C. (heating rate: 10° C./min) and a calcinating time of 6 hours, and air cooling was then conducted. Thereafter, calcined particles, which were an air-cooled calcined product of the dried granules, were subjected to a dry grinding treatment by means of the centrifugal grinder "ZM100" (manufactured by NIHONSEIKI KAISHA LTD.), in which a mesh having a screen diameter of 1.5 mm had been set, under conditions of a rotating speed of 14,000 rpm, thereby obtaining titanium dioxide particles (hereinafter also referred to as "comparative titanium dioxide particles (H)").

The median diameter and BET specific surface area of the resultant comparative titanium dioxide particles (H) were measured and found to be 6.6 μm and 24.1 m$^2$/g, respectively.

Example 1

Preparation Example of Formed Material of Bone Cement Composition

A Henschel mixer "IMC-1857" (manufactured by IMOTO MACHINERY CO., LTD.) was used to mix 8.82 g of the titanium dioxide particles (A), 32.34 g of polymethyl methacrylate powder (average particle diameter: 35 μm, average molecular weight: 150,000, particle shape: spherical; product of SEKISUI PLASTICS CO., LTD.) and 0.882 g of benzoyl peroxide (product of KAWAGUCHI CHEMICAL CO., LTD.) for 3 minutes under conditions of a rotating speed of 1,000 rpm, and the resultant mixture was subjected to a degassing treatment for 1 hour by means of a vacuum pump, thereby obtaining a mixed powder component.

On the other hand, 0.2058 g of N,N-dimethyl-p-toluidine (product of Mitsuboshi Chemical Co., Ltd.) was added to 17.64 g of methyl methacrylate (product of MITSUBISHI GAS CHEMICAL COMPANY, INC.) to mix them for 5 minutes by means of a stirrer, thereby obtaining a mixed liquid component.

The resultant mixed powder component and mixed liquid component were stored in separate containers, thereby preparing a bone cement composition kit (hereinafter also referred to as "the bone cement composition kit (1)") made up of a polymerization initiator-containing kit component composed of the mixed powder component and a monomer-containing kit component composed of the mixed liquid component.

In this bone cement composition kit (1), the content of the titanium dioxide particles (A) was 15% by mass (the content based on the total content with the (meth)acrylate polymer being 21.4% by mass), and the content of the (meth)acrylate polymer composed of the polymethyl methacrylate powder based on the total mass of the base-forming component was 64.7% by mass. The content of the (meth)acrylate monomer composed of methyl methacrylate was 29.5% by mass based on the total mass of the composition. The proportion of the polymerization initiator composed of benzoyl peroxide to the (meth)acrylate monomer was 5.0% by mass, and the proportion of the polymerization accelerator composed of N,N-dimethyl-p-toluidine to the (meth)acrylate monomer was 1.17% by mass.

After the polymerization initiator-containing kit component of the bone cement composition kit (1) was put in a kneading container made of polytetrafluoro-ethylene, the monomer-containing kit component of the bone cement composition kit (1) was poured therein, thereby obtaining a bone cement composition, and this bone cement composition was kneaded for 1 minute under a degassed atmosphere formed by suction for 30 seconds under ordinary pressure. The resultant kneaded product was cast in a polytetrafluoroethylene-made jig for preparing a specimen for measurement of flexural strength, and a lid was closed after confirming that the flowability of the kneaded product became small to leave the kneaded product at rest for at least 24 hours under an environment of 30° C. in temperature, thereby obtaining a formed material (hereinafter also referred to as "the bone cement formed material (1)") composed of a hardened material of the bone cement composition.

Here, the content of the titanium dioxide particles in the resultant bone cement formed material (1) was 15% by mass.
(Measurement of Flexural Strength)

The resultant bone cement formed material (1) was subjected to a wet polishing treatment using #400 polishing paper so as to give a size of 75 mm×10 mm×3.3 mm, thereby conducting the measurement of flexural strength according to the measuring method based on ISO 5833. The result is shown in the following Table 1.

Example 2 to Example 6

Bone cement composition kits were obtained in the same manner as in Example 1 except that the titanium dioxide particles (B) to the titanium dioxide particles (F) were respectively used in place of the titanium dioxide particles (A) in Preparation Example of formed material of bone cement composition in Example 1, and the bone cement composition kits were used to obtain formed materials (hereinafter also referred to as "the bone cement formed material (2)" to "the bone cement formed material (6)", respectively) respectively composed of hardened materials of the bone cement compositions.

With respect to each of the resultant bone cement formed material (2) to bone cement formed material (6), its flexural strength was measured by the same method as in Example 1. The results are shown in the following Table 1.

Comparative Example 1

A bone cement composition kit was obtained in the same manner as in Example 1 except that rutile-type titanium dioxide "CR-EL" (product of ISHIHARA. SANGYO KAISHA, LTD.) was used in place of the titanium dioxide particles (A) in Preparation Example of formed material of bone cement composition in Example 1, and the bone cement composition kit was used to obtain a formed material (hereinafter also referred to as "the comparative bone cement formed material (1)") composed of a hardened material of the bone cement composition.

With respect to the resultant comparative bone cement formed material (1), its flexural strength was measured by the same method as in Example 1. The result is shown in the following Table 1.

Here, the median diameter and BET specific surface area of the rutile-type titanium dioxide "CR-EL" (product of ISHIHARA SANGYO KAISHA, LTD.) were measured and found to be 1.0 μm and 7.35 m$^2$/g, respectively.

Comparative Example 2 and Comparative Example 3

Bone cement composition kits were obtained in the same manner as in Example 1 except that the comparative titanium dioxide particles (G) and the titanium dioxide particles (H) were respectively used in place of the titanium dioxide particles (A) in Preparation Example of formed material of bone cement composition in Example 1, and the bone cement composition kits were used to obtain formed materials (hereinafter also referred to as "the comparative bone cement formed material (2)" and "the comparative bone cement formed material (3)", respectively) respectively composed of hardened materials of the bone cement compositions.

With respect to each of the resultant comparative bone cement formed material (2) to comparative bone cement formed material (3), its flexural strength was measured by the same method as in Example 1. The results are shown in the following Table 1.

TABLE 1

| | | Titanium dioxide particles | | | |
|---|---|---|---|---|---|
| | | Kinds | Median diameter (μm) | BET specific surface areas (m$^2$/g) | Flexural strength (MPa) |
| Example 1 | Bone cement formed body (1) | Titanium dioxide particles (A) | 2.3 | 2.02 | 81.3 |
| Example 2 | Bone cement formed body (2) | Titanium dioxide particles (B) | 2.9 | 1.90 | 85.4 |
| Example 3 | Bone cement formed body (3) | Titanium dioxide particles (C) | 5.1 | 0.85 | 86.0 |
| Example 4 | Bone cement formed body (4) | Titanium dioxide particles (D) | 6.4 | 0.59 | 90.0 |
| Example 5 | Bone cement formed body (5) | Titanium dioxide particles (E) | 1.2 | 3.40 | 61.6 |
| Example 6 | Bone cement formed body (6) | Titanium dioxide particles (F) | 0.7 | 6.73 | 61.9 |
| Comparative Example 1 | Comparative Bone cement formed body (1) | Rutile-type Titanium dioxide "CR-EL" | 1.0 | 7.35 | 56.7 |
| Comparative | Comparative | Comparative | 3.4 | 30.6 | 54.5 |

TABLE 1-continued

| | | | Titanium dioxide particles | | |
|---|---|---|---|---|---|
| | | Kinds | Median diameter (μm) | BET specific surface areas (m²/g) | Flexural strength (MPa) |
| Example 2 | Bone cement formed body (2) | Titanium dioxide particles (G) | | | |
| Comparative Example 3 | Comparative Bone cement formed body (3) | Comparative Titanium dioxide particles (H) | 6.6 | 24.1 | 58.3 |

From the results shown in Table 1, it was confirmed that all the bone cement formed material (1) to the bone cement formed material (6) according to Example 1 to Example 6 have flexural strength of at least 60 MPa, and so high mechanical strength practically required is achieved therein.

In particular, it was confirmed that all the bone cement formed material (1) to the bone cement formed material (4) according to Example 1 to Example 4 have flexural strength of at least 80 MPa, and so extremely high mechanical strength is achieved therein.

On the other hand, in the comparative bone cement formed material (1) to the comparative bone cement formed material (3) according to Comparative Example 1 to Comparative Example 3, it was confirmed that sufficient mechanical strength practically required is not achieved because the BET specific surface areas of the titanium dioxide particles contained therein are all too large.

Preparation Example 7 of Titanium Dioxide Particles

Titanium dioxide particles (hereinafter also referred to as "titanium dioxide particles (I)") were obtained in the same manner as in Preparation Example 1 of titanium dioxide particles except that a mixed slurry of the grinding treatment-subjected titanic acid slurry and the rutile dislocation-accelerating seed slurry was prepared so as to give a titanium dioxide concentration of 4.0% by mass in Spray drying process in Preparation Example 1 of titanium dioxide particles, thereby obtaining a slurry for spray drying treatment, and dried granules having a median diameter of 3.4 μm were obtained as a cyclone product.

The median diameter and BET specific surface area of the resultant titanium dioxide particles (I) were measured and found to be 3.4 μm and 1.24 m²/g, respectively.

From a result of powder X-ray diffraction using the powder X-ray diffractometer "RINT 1200" (manufactured by Rigaku Corporation), it was confirmed that the titanium dioxide particles (I) are rutile-type titanium dioxide particles, and from a result of observation through the electron microscope, it was confirmed that the shape thereof is spherical.

Example 7 to Example 10

Bone cement composition kits were obtained in the same manner as in Example 2 except that the titanium dioxide particles (I) were used in place of the titanium dioxide particles (B) in Preparation Example of formed material of bone cement composition in Example 2, and the used amounts of the titanium dioxide particles (I) and the polymethyl methacrylate powder (average particle diameter: 35 μm, average molecular weight: 150,000, particle shape: spherical; product of SEKISUI PLASTICS CO., LTD.) were changed to their corresponding amounts shown in the following Table 2. The bone cement composition kits were used to obtain formed materials (hereinafter also referred to as "the bone cement formed material (7)" to "the bone cement formed material (10)", respectively) respectively composed of hardened materials of the bone cement compositions. Incidentally, in the preparation of each of the bone cement composition kits used for obtaining the bone cement formed material (7) to the bone cement formed material (10), 17.64 g (29.5% by mass) of methyl methacrylate, 0.882 g (proportion to the (meth)acrylate monomer: 5.0% by mass) of benzoyl peroxide and 0.2058 g (proportion to the (meth)acrylate monomer: 1.17% by mass) of N,N-dimethyl-p-toluidine were used.

With respect to each of the resultant bone cement formed material (7) to bone cement formed material (10), its flexural strength was measured by the same method as in Example 1. The results are shown in the following Table 2.

Preparation Example 8 of Titanium Dioxide Particles

Titanium dioxide particles (hereinafter also referred to as "titanium dioxide particles (J)") were obtained in the same manner as in Preparation Example 2 of titanium dioxide particles except that an orthotitanic acid slurry (grinding treatment-subjected titanic acid slurry), the titanium dioxide concentration in the orthotitanic acid of which was 8.34% by mass, was obtained in Preparation of titanic acid slurry and Wet grinding process in Preparation Example 2 of titanium dioxide particles, a mixed slurry of the grinding treatment-subjected titanic acid slurry and the rutile dislocation-accelerating seed slurry was prepared so as to give a titanium dioxide concentration of 3.0% by mass in Spray drying process, thereby obtaining a slurry for spray drying treatment, and the conditions of the air flow rate in the spray drying treatment were changed to 90 L/min.

The median diameter and BET specific surface area of the resultant titanium dioxide particles (J) were measured and found to be 2.6 μm and 2.83 m²/g, respectively.

From a result of powder X-ray diffraction using the powder X-ray diffractometer "RINT 1200" (manufactured by Rigaku Corporation), it was confirmed that the titanium dioxide particles (J) are rutile-type titanium dioxide particles, and from a result of observation through the electron microscope, it was confirmed that the shape thereof is spherical.

Example 11

A bone cement composition kit was obtained in the same manner as in Example 1 except that the titanium dioxide particles (J) were used in place of the titanium dioxide particles (A) in Preparation Example of formed material of bone cement composition in Example 1, the used amount thereof was changed to 17.64 g, and the used amount of the polymethyl methacrylate powder was changed to 23.520 g, and the bone cement composition kit was used to obtain a formed material (hereinafter also referred to as "the bone cement formed material (11)") composed of a hardened material of the bone cement composition. Incidentally, in the preparation of the bone cement composition kit used for obtaining the bone cement formed material (11), 17.64 g (29.5% by mass) of methyl methacrylate, 0.882 g (proportion to the (meth)acrylate monomer: 5.0% by mass) of benzoyl peroxide and 0.2058 g (proportion to the (meth)acrylate monomer: 1.17% by mass) of N,N-dimethyl-p-toluidine were used.

In the bone cement composition kit related to the bone cement formed material (11), the proportion of the (meth)acrylate polymer composed of the polymethyl methacrylate powder contained in the whole base-forming component was 57.1% by mass.

With respect to each of the resultant one cement formed material (11), its flexural strength was measured by the same method as in Example 1. The result is shown in the following Table 2.

cement composition "Surgical Simplex P" was used as the bone cement composition in Example 12 to conduct the adhesive strength test. The results are illustrated in FIG. 1.

Here, the bone cement composition "Surgical Simplex P" contains 6.8% by mass of barium sulfate, 10.2% by mass of polymethyl methacrylate, 51.0% by mass of a polymethyl methacrylate-styrene copolymer, 31.2% by mass of methyl methacrylate and 0.8% by mass of N,N-dimethyl-p-toluidine. In this bone cement composition, the proportion of the (meth)acrylate polymer composed of the polymethyl methacrylate powder and the polymethyl methacrylate-styrene copolymer contained in the whole base-forming component was 66.3% by mass, the proportion of the polymerization accelerator composed of N,N-dimethyl-p-toluidine to the (meth)acrylate monomer is 2.49% by mass.

TABLE 2

| | | Bone cement composition kit | | | | |
| | | Titanium dioxide particles | | PMMA | | |
| | | Kinds | Used amouts (g) | Proportion in the total composition (wt %) | Used amouts (g) | Proportion in the base-forming component (wt %) | Flexural strength (MPa) |
|---|---|---|---|---|---|---|---|
| Example 7 | Bone cement formed body (7) | Titanium dioxide particles (I) | 2.94 | 5 | 38.220 | 68.4 | 76.4 |
| Example 8 | Bone cement formed body (8) | Titanium dioxide particles (I) | 5.88 | 10 | 35.328 | 66.7 | 77.6 |
| Example 9 | Bone cement formed body (9) | Titanium dioxide particles (I) | 8.82 | 15 | 32.340 | 64.7 | 87.4 |
| Example 10 | Bone cement formed body (10) | Titanium dioxide particles (I) | 11.75 | 20 | 29.410 | 62.5 | 72.2 |
| Example 11 | Bone cement formed body (11) | Titanium dioxide particles (J) | 17.64 | 30 | 23.520 | 57.1 | 60.2 |

From the results shown in Table 2, it was confirmed that when the content of the titanium dioxide particles is 5 to 30% by mass, sufficient mechanical strength practically required is achieved.

Example 12

A hardened material prepared by using a bone cement composition composed of 15% by mass of the titanium dioxide particles (J), 55% by mass (proportion in the base-forming component, i.e., proportion to the total amount of the polymethyl methacrylate powder and methyl methacrylate: 64.7% by mass) of polymethyl methacrylate powder (average particle diameter: 33.9 μm, average molecular weight (Mw): 141,000, particle shape: spherical, 30% by mass of methyl methacrylate, 1.5% by mass of benzoyl peroxide and 0.35% by mass of N,N-dimethyl-p-toluidine was inserted into bores 2.5 mm in diameter formed in the femurs of male Japanese white rabbits (weight: 3.0 to 3.5 kg, available from KITAYAMA LABES CO., LTD.). After 6 weeks and 12 weeks, the rabbits were subjected to pathological autopsy to measure adhesive strength. The results are illustrated in FIG. 1.

The measurement of the adhesive strength was conducted by using "Bone Strength Testing System CTR-Win" (manufactured by MARUTO INSTRUMENT CO., LTD.) as a measuring instrument to calculate adhesive strength based on a load (testing force) at the time the hardened material and the bone (femur) were broken under conditions of a crosshead speed of 1 mm/min according to the push out method.

Comparative Example 4

A hardened material was prepared in the same manner as in Example 12 except that a commercially available bone From the results illustrated in FIG. 1, it was confirmed that since adhesive strength superior to the hardened material according to Comparative Example 4 is achieved in the hardened material according to Example 12 after 6 weeks and 12 weeks, the composition of Example 12 has excellent bioactivity compared with the commercially available bone cement composition.

The invention claimed is:

1. A bone cement composition comprising:
   titanium dioxide particles having a median diameter of 0.5 to 7.0 μm as measured by a laser diffraction/scattering particle size distribution analyzer and a BET specific surface area of 0.5 to 7.0 m$^2$/g as measured by a nitrogen adsorption method; and
   a base-forming component comprising a (meth)acrylate polymer and a (meth)acrylate monomer,
   wherein the content of the titanium dioxide particles is 5 to 50% by mass based on a total mass of the composition and wherein the titanium dioxide particles are subjected to an acid-washing treatment.

2. The bone cement composition according to claim 1, wherein a median diameter and a BET specific surface area of the titanium dioxide particles are 1.5 to 7.0 μm and 0.5 to 5.0 m$^2$/g, respectively.

3. The bone cement composition according to claim 1, wherein the titanium dioxide particles are rutile titanium dioxide particles.

4. The bone cement composition according to claim 1, wherein the titanium dioxide particles are spherical.

5. The bone cement composition according to claim 1, wherein the titanium dioxide particles are produced by performing steps of subjecting a slurry of titanic acid to a spray drying treatment, thereby obtaining dried granules, and subjecting the dried granules to a calcinating treatment.

6. The bone cement composition according to claim 1, wherein the content of the (meth)acrylate polymer making up the base-forming component is 30 to 80% by mass based on a total mass of the base-forming component.

7. The bone cement composition according to claim 1, further comprising a polymerization initiator.

8. The bone cement composition according to claim 1, wherein the bone cement composition is hardened by polymerizing the (meth)acrylate monomer in vivo.

9. A bone cement composition kit for obtaining the bone cement composition according to claim 8, comprising a monomer-containing kit component containing at least a (meth)acrylate monomer among titanium dioxide particles, a (meth)acrylate polymer, the (meth)acrylate monomer and a polymerization initiator, and a polymerization initiator-containing kit component containing at least the polymerization initiator.

10. The bone cement composition kit according to claim 9, wherein the polymerization initiator-containing kit component contains the titanium dioxide particles and the (meth)acrylate polymer together with the polymerization initiator.

11. A bone cement formed material comprising:
   titanium dioxide particles having a median diameter of 0.5 to 7.0 μm as measured by a laser diffraction/scattering particle size distribution analyzer and a BET specific surface area of 0.5 to 7.0 $m^2/g$ as measured by a nitrogen adsorption method; and
   a base component comprising a (meth)acrylate polymer,
   wherein the content of the titanium dioxide particles is 5 to 50% by mass and wherein the titanium dioxide particles are subjected to an acid-washing treatment.

12. The bone cement formed material according to claim 11, wherein the median diameter and the BET specific surface area of the titanium dioxide particles are 1.5 to 7.0 μm and 0.5 to 5.0 $m^2/g$, respectively.

13. The bone cement formed material according to claim 11, wherein the titanium dioxide particles are rutile titanium dioxide particles.

14. The bone cement formed material according to claim 11, wherein the titanium dioxide particles are spherical.

15. The bone cement formed material according to claim 11, wherein the titanium dioxide particles are produced by performing steps of subjecting a slurry of titanic acid to a spray drying treatment, thereby obtaining dried granules, and subjecting the dried granules to a calcinating treatment.

16. The bone cement formed material according to claim 11, which has a flexural strength of at least 70 MPa as measured according to measuring method ISO 5833 prescribed by ISO standards.

17. The bone cement formed material according to claim 11, wherein the bone cement formed material is used as an artificial bone.

18. A production method of a bone cement formed material, comprising:
   a polymerization step of polymerizing a (meth)acrylate monomer with a polymerization initiator in the presence of titanium dioxide particles having a median diameter of 0.5 to 7.0 μm as measured by a laser diffraction/scattering particle size distribution analyzer and a BET specific surface area of 0.5 to 7.0 $m^2/g$ as measured by a nitrogen adsorption method and a (meth)acrylate polymer, thereby obtaining a bone cement formed material containing the titanium dioxide particles and a base component comprising the (meth)acrylate polymer,
   wherein the content of the titanium dioxide particles is 5 to 50% by mass based on a total mass of the formed material and wherein the titanium dioxide particles are subjected to an acid-washing treatment.

19. The production method according to claim 18, wherein the polymerization initiator is benzoyl peroxide.

20. The production method according to claim 18, wherein a polymerization accelerator is used in the polymerization step.

21. The production method according to claim 18 wherein an amount of the (meth)acrylate polymer used in the polymerization step is 30 to 80% by mass based on a total mass of the amount of the (meth)acrylate polymer used and an amount of the (meth)acrylate monomer used in the polymerization step.

22. The production method according to claim 18, wherein the formed material is formed in the polymerization step.

* * * * *